United States Patent
Clozel

(10) Patent No.: US 9,597,331 B2
(45) Date of Patent: *Mar. 21, 2017

(54) THERAPEUTIC COMPOSITIONS CONTAINING MACITENTAN

(71) Applicant: ACTELION PHARMACEUTICALS LTD, Allschwil (CH)

(72) Inventor: Martine Clozel, Binningen (CH)

(73) Assignee: ACTELION PHARMACEUTICALS LTD., Allschwil (CH)

(*) Notice: Subject to any disclaimer, the term of this patent is extended or adjusted under 35 U.S.C. 154(b) by 0 days.

This patent is subject to a terminal disclaimer.

(21) Appl. No.: 14/873,787

(22) Filed: Oct. 2, 2015

(65) Prior Publication Data

US 2016/0022678 A1 Jan. 28, 2016

Related U.S. Application Data

(63) Continuation of application No. 14/335,657, filed on Jul. 18, 2014, now Pat. No. 9,173,881, which is a continuation of application No. 13/058,639, filed as application No. PCT/IB2009/053553 on Aug. 12, 2009, now Pat. No. 8,809,334.

(30) Foreign Application Priority Data

Aug. 13, 2008 (WO) .................. PCT/IB2008/053252

(51) Int. Cl.
| | |
|---|---|
| A61K 31/506 | (2006.01) |
| A61K 31/5578 | (2006.01) |
| A61K 31/343 | (2006.01) |
| A61K 31/4965 | (2006.01) |
| A61K 31/5575 | (2006.01) |
| A61K 45/06 | (2006.01) |

(52) U.S. Cl.
CPC .......... *A61K 31/506* (2013.01); *A61K 31/343* (2013.01); *A61K 31/4965* (2013.01); *A61K 31/5575* (2013.01); *A61K 31/5578* (2013.01); *A61K 45/06* (2013.01)

(58) Field of Classification Search
IPC ....................................... A61K 31/506,31/5578
See application file for complete search history.

(56) References Cited

U.S. PATENT DOCUMENTS

| | | | |
|---|---|---|---|
| 4,474,802 A | 10/1984 | Ohno et al. | |
| 4,539,333 A | 9/1985 | Moncada | |
| 4,683,330 A | 7/1987 | Aristoff | |
| 4,692,464 A | 9/1987 | Skuballa et al. | |
| 7,094,781 B2 | 8/2006 | Bolli et al. | |
| 7,205,302 B2 | 4/2007 | Asaki et al. | |
| 7,285,549 B2 | 10/2007 | Bolli et al. | |
| 7,452,896 B2 | 11/2008 | Bolli et al. | |
| 7,868,012 B2 | 1/2011 | Bolli et al. | |
| 8,268,847 B2 | 9/2012 | Clozel et al. | |
| 8,367,685 B2 | 2/2013 | Adesuyi et al. | |
| 8,541,433 B2 | 9/2013 | Clozel et al. | |
| 8,809,334 B2 | 8/2014 | Clozel et al. | |
| 9,173,881 B2 | 11/2015 | Clozel et al. | |
| 2005/0101608 A1* | 5/2005 | Santel ................. | A61K 45/06 |
| | | | 514/252.16 |
| 2008/0233188 A1 | 9/2008 | Adesuyi et al. | |
| 2013/0005734 A1 | 1/2013 | Clozel | |
| 2013/0190336 A1 | 7/2013 | Adesuyi | |
| 2013/0317048 A1 | 11/2013 | Clozel et al. | |
| 2014/0148460 A1 | 5/2014 | Clozel | |
| 2016/0136163 A1 | 5/2016 | Adesuyi et al. | |

FOREIGN PATENT DOCUMENTS

| WO | WO 02/053557 A1 | 7/2002 |
|---|---|---|
| WO | WO 2004/017993 A1 | 3/2004 |
| WO | WO 2005/030187 A2 | 4/2005 |

OTHER PUBLICATIONS

Higenbottam et al. (heart 79; 175-179 (1998).*
Iglaz et al. (The J. of Pharmacology and Exp. Therapeutics, 327(3); (2008).*
Battistini, et al. "Profile of Past and Current Clinical Trials Involving Endothelin Receptor Antagonists: The Novel "-Sentan" Class of Drug"; Exp. Biol. Med., vol. 231, No. 6, pp. 653-695; (2006).
CAS Registry Record for Macitentan (entered STN: Aug. 1, 2002).
Gould, P., L., "Salt Selection for Basic Drugs", International Journal of Pharmaceutics, vol. 33, pp. 201-217, (1986).
Hoeper, M.M. et al., "New Treatments for Pulmonary Arterial Hypertension", American Journal of Respiratory and Critical Care Medicine, American Lung Association, 2002, vol. 165, pp. 1209-1216.
Kunio Hiwada, "The Growing Need for Combination Therapy", MEBIO, 1999, vol. 16, No. 9, pp. 87-90 (Japanese Article and English translation).
Kuwano, K., et al., "2-{4-[(5,6-Diphenylpyrazin-2-yl)(isopropyl)amino]butoxy}-N-(methylsulfonyl)acetamide NS-304), an Orally Available and Long-Acting Prostacyclin Receptor Agonist Prodrug", The Journal of Pharmacology and Experimental Therapeutics, vol. 322, No. 3, pp. 1181-1188, (2007).

(Continued)

*Primary Examiner* — Shirley V Gembeh
(74) *Attorney, Agent, or Firm* — Hoxie & Associates LLC

(57) ABSTRACT

The invention relates to a product containing the compound of formula (I) below or a pharmaceutically acceptable salt of this compound, in combination with at least one compound having prostacyclin receptor (IP) agonist properties, or a pharmaceutically acceptable salt thereof.

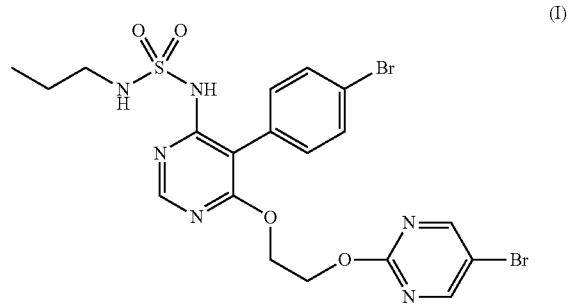

(I)

13 Claims, No Drawings

(56) References Cited

OTHER PUBLICATIONS

Kuwano, K. et al., A Long-Acting and Highly Selective Prostacyclin Receptor Agonist Prodrug, 2-{4-[(5,6-Diphenylpyrazin-2-yl)(isopropyl)amino]butoxy}-N-(methylsulfonyl)acetamide (NS-304), Ameliorates Rat Pulmonary Hypertension with Unique Relaxant Responses of Its Active Form, {4-[(5,6-Diphenylpyrazin-2-yl)(isopropyl)amino]butoxy} acetic Acid (MRE-269), on Rat Pulmonary Artery; The Journal of Pharmacology and Experimental Therapeutics; vol. 326, No. 3; pp. 691-699; 2008.

Mclaughlin, V.V. et al., "Randomized Study of Adding Inhales Iloprost to Existing Bosentan in Pulmonary Arterial Hypertension", American Journal of Respiratory and Critical Care Medicine, vol. 174, pp. 1257-1263, (2006).

Motte, S. et al., "Endothelin Receptor Antagonists", Pharmacology and Therapeutics, vol. 110, pp. 386-414, (2006).

Senior, J. et al., "In Vitro Characterization of Prostanoid FP-, DP-, IP-, and TP-Receptors on the Non-Pregnant Human Myometrium", Br. J. Pharmacol., vol. 107, pp. 215-221, (1992).

Sidharta, P. N., et al., "Pharmacokinetics and Pharmacodynamics of the Endothelin-1 Receptor Antagonist Act-064992 in Healthy Human Subjects", Journal of Clinical Pharmacology, vol. 47, No. 9, p. 1202, 2007. (Abstract).

Ueno, M., et al., "A Combination of Oral Endothelin-A Receptor Antagonist and Oral Prostacyclin Analogue is Superior to Each Drug Alone in Ameliorating Pulmonary Hypertension in Rats", Journal of the American College of Cardiology, vol. 40, No. 1, pp. 175-181, (2002).

WHO Drug Information; "International Nonproprietary Names for Pharmaceutical Substances (INN)"; Proposed INN: 2008, List 99, vol. 22, No. 2, pp. 121-122, 142-143.

Notice of Allowance of U.S. Appl. No. 12/388,142 dated Sep. 25, 2012.

Response Filed Jan. 29, 2014 in European Patent Application No. 09786912 (EP09786912.7).

* cited by examiner

THERAPEUTIC COMPOSITIONS CONTAINING MACITENTAN

CROSS REFERENCE TO RELATED APPLICATIONS

This application is a continuation application of U.S. Ser. No. 14/335,657, filed on Jul. 18, 2014, which application is a continuation application of U.S. Ser. No. 13/058,639, filed on Feb. 11, 2011, which application is a national stage of PCT Application No. PCT/IB2009/053553, filed on Aug. 12, 2009, which claims the benefit of PCT Application No. PCT/IB2008/053252, filed on Aug. 13, 2008, the contents of each of which are incorporated herein by reference.

The present invention relates to a product containing macitentan, i.e. the compound of formula (I) below

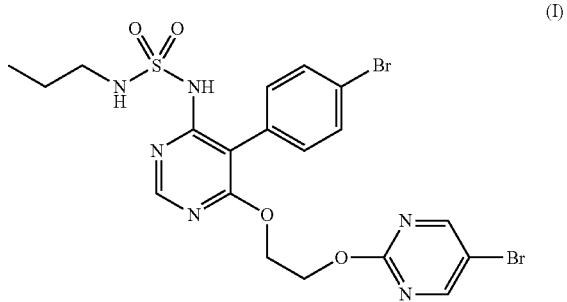 [SMILES: CCCNS(=O)(=O)Nc1ncnc(OCCOc2ncc(Br)cn2)c1-c1ccc(Br)cc1]

(I)

or a pharmaceutically acceptable salt of this compound, in combination with at least one compound having prostacyclin receptor (IP) agonist properties, or a pharmaceutically acceptable salt thereof, as well as this product for therapeutic use, simultaneously, separately or over a period of time, in the treatment of a disease wherein endothelin is involved.

PCT publication WO 02/053557 describes endothelin receptor antagonists including the compound of formula (I) and the use of said endothelin receptor antagonists in the treatment of various diseases wherein endothelin is involved (i.a. heart failure, angina pectoris, pulmonary and systemic hypertension and erectile dysfunction).

Compounds having prostacyclin receptor (IP) agonist properties have been described notably in the following documents:
- U.S. Pat. No. 4,683,330 describe the compound treprostinil and salts and analogues thereof;
- U.S. Pat. No. 4,539,333 describes epoprostenol sodium;
- U.S. Pat. No. 4,692,464 describe the compound iloprost and salts and analogues thereof;
- U.S. Pat. No. 4,474,802 describe the compound beraprost and salts and analogues thereof;
- U.S. Pat. No. 7,205,302 describe among others 5,6-diphenylpyrazine derivatives having prostacyclin receptor (IP) agonist properties, and salts and analogues thereof, an in particular the compounds known under the code names MRE-269 and NS-304 (K. Kuwano et al., *J. Pharmacol. Exp. Ther.* (2007), 322(3), 1181-1188).

Besides, WO 2004/017993 describes the use of the endothelin receptor antagonist bosentan together with the prostacyclin receptor agonist epoprostenol sodium for treating pulmonary arterial hypertension.

The Applicant has now found that the combination of macitentan with a compound having prostacyclin receptor (IP) agonist properties results in a strong synergistic effect in the treatment of diseases wherein endothelin is involved.

Additionally, the possible side effects related to the compounds having prostacyclin receptor (IP) agonist properties (e.g. flushing or systemic hypotension) are expected to be decreased.

A first subject of this invention relates thus to a product containing macitentan or a pharmaceutically acceptable salt thereof, and at least one (and preferably one) compound having prostacyclin receptor (IP) agonist properties, or a pharmaceutically acceptable salt thereof.

A further subject of this invention is a product containing macitentan or a pharmaceutically acceptable salt thereof, in combination with at least one (and preferably one) compound having prostacyclin receptor (IP) agonist properties, or a pharmaceutically acceptable salt thereof, for therapeutic use, simultaneously, separately or over a period of time, in the treatment of a disease wherein endothelin is involved.

The following paragraphs provide definitions of the various terms used in the present patent application and are intended to apply uniformly throughout the specification and claims, unless an otherwise expressly set out definition provides a broader or narrower definition.

Macitentan is the recommended INN for the compound of formula (I) and this name will therefore be used to designate the compound of formula (I) in the present patent application.

"Simultaneously" or "simultaneous", when referring to a therapeutic use, means in the present application that the therapeutic use concerned consists in the administration of two or more active ingredients by the same route and at the same time.

"Separately" or "separate", when referring to a therapeutic use, means in the present application that the therapeutic use concerned consists in the administration of two or more active ingredients at approximately the same time by at least two different routes.

By therapeutic administration "over a period of time" is meant in the present application the administration of two or more ingredients at different times, and in particular an administration method according to which the entire administration of one of the active ingredients is completed before the administration of the other or others begins. In this way it is possible to administer one of the active ingredients for several months before administering the other active ingredient or ingredients. In this case, no simultaneous administration occurs. Another therapeutic administration over a period of time consists in the administration over time of the two or more active ingredients of the combination using different frequencies of administration for each of the active ingredients, whereby at certain points in time simultaneous administrations of all the active ingredients of the combination take place whereas at some other points in time only part of the active ingredients of the combination may be administered (for example, in the case of a combination of macitentan with NS-304, the therapeutic administration over a period of time could be such that macitentan will be administered once a day whereas NS-304 will be administered twice a day).

By "disease wherein endothelin is involved" is meant in particular hypertension, pulmonary hypertension (including pulmonary arterial hypertension), diabetic arteriopathy, heart failure, erectile dysfunction, angina pectoris or pulmonary fibrosis.

By "compound having prostacyclin receptor (IP) agonist properties" is meant a compound that, when submitted to the "Test for the determination of prostacyclin receptor (IP)

agonist EC$_{50}$" described in the present patent application, has an EC$_{50}$ value equal to or lower than 500 nM.

Specific examples of compounds having prostacyclin receptor (IP) agonist properties include treprostinil and its pharmaceutically acceptable salts, epoprostenol and its pharmaceutically acceptable salts, iloprost and its pharmaceutically acceptable salts, beraprost and its pharmaceutically acceptable salts, 2-{4-[(5,6-diphenylpyrazin-2-yl)(isopropyl)amino]butoxy}-N-(methylsulfonyl)acetamide (NS-304) and its pharmaceutically acceptable salts, and {4-[(5,6-diphenylpyrazin-2-yl)(isopropyl)amino]butoxy}acetic acid (MRE-269) and its pharmaceutically acceptable salts.

The term "pharmaceutically acceptable salts" refers to non-toxic, inorganic or organic acid and/or base addition salts. Reference can be made to "Salt selection for basic drugs", Int. J. Pharm. (1986), 33, 201-217.

Besides, any reference to macitentan or to a compound having prostacyclin receptor (IP) agonist properties is to be understood as referring also to the pharmaceutically acceptable salts thereof, as appropriate and expedient.

Preferably, the product according to this invention will be such that macitentan and the compound having prostacyclin receptor (IP) agonist properties are intended for a therapeutic use which takes place simultaneously or over a period of time.

According to one preferred variant of this invention, macitentan and the compound having prostacyclin receptor (IP) agonist properties will be intended to be administered simultaneously.

According to another preferred variant of this invention, macitentan and the compound having prostacyclin receptor (IP) agonist properties will be intended to be administered over a period of time.

The period of time intended for the therapeutic use of a product according to this invention will be at least one week, and preferably at least one or more months (for example six months). This period of time may also be the whole life of the patient that receives the product. According to a particular mode of administration according to this invention, administration of macitentan will be alternated with administration of a compound having prostacyclin receptor (IP) agonist properties, and the interval between such administration will not exceed two or three days (and more preferably not exceed one day). According to another particular mode of administration according to this invention, in the case of a combination of macitentan with NS-304, the therapeutic administration over a period of time could be such that macitentan will be administered once a day whereas NS-304 will be administered twice a day.

Preferably, the compound having prostacyclin receptor (IP) agonist properties will be selected from 2-{4-[(5,6-diphenylpyrazin-2-yl)(isopropyl)amino]butoxy}-N-(methylsulfonyl)acetamide (NS-304) and its pharmaceutically acceptable salts, and {4-[(5,6-diphenylpyrazin-2-yl)(isopropyl)amino]butoxy}acetic acid (MRE-269) and its pharmaceutically acceptable salts. According to one particularly preferred variant of the invention the compound having prostacyclin receptor (IP) agonist properties will be 2-{4-[(5,6-diphenylpyrazin-2-yl)(isopropyl)amino]butoxy}-N-(methylsulfonyl)acetamide (NS-304) or a pharmaceutically acceptable salt thereof.

The administration route of macitentan and that of the compound having prostacyclin receptor (IP) agonist properties is preferably the same. In particular, the common administration route for macitentan and for the compound having prostacyclin receptor (IP) agonist properties will be the oral route.

Though the exact administration doses of a product according to this invention will have to be determined by the treating physician, it is expected that a dose of 0.05 to 2 mg (and preferably 0.1 to 1 mg) of macitentan per kg of patient body weight and per day will be appropriate. Similarly, it is expected that a dose of 0.5 to 30 µg (and preferably 1.5 to 15 µg) of compound having prostacyclin receptor (IP) agonist properties per kg of patient body weight given twice a day will be appropriate.

Preferably, the disease intended to be treated by a product according to this invention will be selected from hypertension, pulmonary hypertension, diabetic arteriopathy, heart failure, erectile dysfunction, angina pectoris and pulmonary fibrosis. More preferably, the disease intended to be treated by a product according to this invention will be selected from hypertension and pulmonary hypertension. In particular, the disease intended to be treated by a product according to this invention will be pulmonary hypertension (and notably pulmonary arterial hypertension).

The invention also relates to a pharmaceutical composition containing, as active principles, macitentan or a pharmaceutically acceptable salt of this compound, in combination with at least one (and preferably one) compound having prostacyclin receptor (IP) agonist properties, or a pharmaceutically acceptable salt thereof, as well as at least one excipient.

The invention further relates to the use of macitentan or a pharmaceutically acceptable salt of this compound, in combination with at least one (and preferably one) compound having prostacyclin receptor (IP) agonist properties, or a pharmaceutically acceptable salt thereof, for the manufacture of a medicament intended to treat a disease wherein endothelin is involved.

Besides, preferences indicated for the product according to this invention of course apply *mutatis mutandis* to the pharmaceutical compositions and uses of this invention.

Particular embodiments of the invention are described in the following Examples, which serve to illustrate the invention in more detail without limiting its scope in any way.

EXAMPLES

To illustrate the usefulness of this invention, the association of macitentan, administered orally at a dose of 10 mg/kg per day, with NS-304, administered orally at a dose of 1 mg/kg twice a day, can be studied in two different hypertension models, namely the pulmonary hypertension monocrotaline rat model and the spontaneously hypertensive rat model. Other associations may of course be tested similarly. The protocols that may be used are detailed in the part entitled "Pharmacological properties of the invention compounds" hereafter.

Pharmacological Properties of the Invention Compounds

Experimental Methods:
The experimental methods described hereafter can be used to show the pharmacological properties of the invention compounds.
Monocrotaline Model of Pulmonary Hypertension in Rats
Male Wistar rats are purchased from Harlan (Netherlands) and maintained under conditions in accordance with local guidelines (Basel-Landschaft cantonal veterinary office). All rats are housed in climate-controlled conditions with a 12:12 hour light:dark cycle, and had free access to chow and water.

A telemetry system is implanted under anaesthesia by inhalation of 2.5% isoflurane (in 70% $O_2$+30% $N_2O$). Under aseptic conditions, a pressure radio-frequency transmitter is implanted into the peritoneal cavity, and a sensing catheter is inserted in the pulmonary artery. The transmitter is sutured to the abdominal musculature and the skin is closed. A receiver platform transforms the radio signal into digitized input, that is sent to a dedicated personal computer (Compaq, Deskpro). Pulmonary arterial blood pressure measurements are calibrated by using an input from an ambient pressure reference. Telemetry units are obtained from Data Sciences (St. Paul, Minn., USA). Monocrotaline (MCT; Sigma Chemicals, St Louis, Mo., USA) is administered as a single subcutaneous (sc) injection (60 mg/kg) in a volume of 3 ml/kg, and control age-matched rats receive an equal volume of saline.

Variant 1: Chronic Effect Assessment:

The animals are randomly assigned to experimental groups, and treatment is initiated within 24 h after MCT injection, for a duration of 4 weeks. Macitentan and the compound having prostacyclin receptor (IP) agonist properties are administered by the oral route. The effects of macitentan, the compound having prostacyclin receptor (IP) agonist properties and their combination on pulmonary arterial blood pressure are measured by collecting data at 5-minute intervals. Hourly means of pulmonary arterial pressure are calculated for each rat. At the end of recording, rats are sacrificed. The heart is removed and weighed, and the ratio of organ weight to body weight (BW) is calculated. The right ventricle (RV) and the left ventricle plus septum are separated and weighed; the ratio RV/BW is used as an index of right ventricular hypertrophy. The lower the ratio RV/BW, the stronger the effect of the item(s) tested for reducing right ventricular hypertrophy.

Variant 2: Acute Effect Assessment:

Four weeks after injection of MCT, the rats become pulmonary hypertensive and the respective effects of a single oral administration of Macitentan, of the compound having prostacyclin receptor (IP) agonist properties and of their combination can be evaluated on mean pulmonary arterial pressure.

Spontaneously Hypertensive Rat Model

The same protocol is used as for the monocrotaline model of pulmonary hypertension in rats, except that spontaneously hypertensive rats (SHR) replace the monocrotaline-treated rats. The SHR rats are purchased from Harlan (Netherlands).

Test for the Determination of Prostacyclin Receptor (IP) Agonist $EC_{50}$:

CHO cells stably expressing the human IP receptor are cultured in Ham's F-12 medium containing 10% fetal bovine serum in a humidified atmosphere of 95% air and 5% $CO_2$ at 37° C. Cells are seeded at $1\times10^5$ cells/well in 24-well plates and cultured for 48 h. Following a wash and incubation with assay buffer for 1 h at 37° C., the cells are exposed to various concentrations of test compound in the presence of IBMX (500 µM). After removal of supernatant, the reaction is stopped by addition of 0.2 M perchloric acid. Adherent cells are frozen for 2 h at −80° C. and thawed to extract intracellular cAMP. Supernatants are collected in tubes, neutralized by 2M $KHCO_3$ solution, and then centrifuged at 14,000 g for 10 min at 4° C. to obtain samples for measurement of cAMP levels by EIA system. Protein content of cell debris adhered to culture plates is measured following solubilization in 1N NaOH solution. Levels of cAMP are expressed as pmol cAMP/mg protein. The $EC_{50}$ value is determined from non-linear regression analyses of concentration-response curves, and is defined as the negative logarithm of the concentration of test compound that elicits a response that is half of the maximal effect observed.

Experimental Results:

Example 1

Acute Effect of Macitentan, NS-304 and Their Combination on Mean Pulmonary Arterial Pressure in Monocrotaline Treated Rats Experiments were performed in pulmonary hypertensive male Wistar rats treated with monocrotaline according to the monocrotaline model as described in the section "Monocrotaline model of pulmonary hypertension in rats" of the part entitled "Experimental methods".

25 to 30 days after the monocrotaline treatment, four groups of 6 rats were formed and studied:

the first group was treated neither with macitentan nor with NS-304 (control group);

the second group was treated with macitentan only (10 mg/kg per os);

the third group was treated neither with NS-304 only (30 mg/kg per os);

the fourth group was treated with a combination of macitentan (10 mg/kg per os) and NS-304 (30 mg/kg per os).

Mean pulmonary arterial pressure was measured over time. The relationship between mean pulmonary arterial pressure and time was plotted as a graph. Area Under Curve (AUC) was calculated for each group of rats after the oral administration of the different treatment(s) (a positive area being found if the mean pulmonary arterial blood pressure increases and a negative area being found if the mean pulmonary arterial blood pressure decreases). The results thus obtained are summarized in Table 1 hereafter.

TABLE 1

| Rat group [treatment] | AUC |
|---|---|
| Group 1 [control: no treatment] | 106 ± 134 |
| Group 2 [treatment with macitentan (10 mg/kg per os)] | −381 ± 147 |
| Group 3 [treatment with NS-304 (30 mg/kg per os)] | −99 ± 128 |
| Group 4 [treatment with macitentan (10 mg/kg per os) and NS-304 (30 mg/kg per os)] | −758 ± 164 |

These data obtained in the monocrotaline model of pulmonary arterial hypertension confirm the synergistic effect of a combination of macitentan and NS-304 in the treatment of rats having previously undergone monocrotaline administration.

The invention claimed is:

1. A method for the treatment of a disease selected from hypertension, pulmonary hypertension, diabetic arteriopathy, heart failure, erectile dysfunction, angina pectoris and pulmonary fibrosis, comprising administering macitentan, in free or pharmaceutically acceptable salt form, in combination with an effective amount of at least one compound having prostacyclin receptor (IP) agonist properties, or a pharmaceutically acceptable salt thereof, wherein the compound having prostacyclin receptor (IP) agonist properties is selected from iloprost and its pharmaceutically acceptable salts.

2. The method according to claim 1, wherein the macitentan and the compound having prostacyclin receptor (IP) agonist properties are administered simultaneously, separately or over a period of time.

3. The method according to claim 2, wherein the macitentan and the compound having prostacyclin receptor (IP) agonist properties are administered simultaneously.

4. The method according to claim 2, wherein the macitentan and the compound having prostacyclin receptor (IP) agonist properties are administered separately.

5. The method according to claim 2, wherein the macitentan and the compound having prostacyclin receptor (IP) agonist properties are administered over a period of time.

6. The method according to claim 1, wherein the disease is pulmonary hypertension.

7. The method according to claim 1, wherein the disease is pulmonary arterial hypertension.

8. The method according to claim 7, wherein the macitentan is in free form.

9. A method for the treatment of pulmonary arterial hypertension comprising administering an effective amount of macitentan in free or pharmaceutically acceptable salt form, in combination with iloprost, in free or pharmaceutically acceptable salt form.

10. The method according to claim 9, wherein the macitentan and the iloprost are administered simultaneously.

11. The method according to claim 9, wherein the macitentan and the iloprost are administered separately.

12. The method according to claim 9, wherein the macitentan and the iloprost are administered over a period of time.

13. The method according to claim 9, wherein the macitentan is administered once a day.

* * * * *